(12) United States Patent
Braun et al.

(10) Patent No.: US 11,879,752 B2
(45) Date of Patent: Jan. 23, 2024

(54) SENSOR MODULE FOR AIR QUALITY MEASUREMENT

(71) Applicant: Sensirion AG, Stäfa (CH)

(72) Inventors: Stephan Braun, Stäfa (CH); Tobias Schmid, Stäfa (CH); Thomas Brugger, Stäfa (CH); Matthias Merz, Stäfa (CH); Manuel Becker, Stäfa (CH)

(73) Assignee: Sensirion AG, Stäfa (CH)

( * ) Notice: Subject to any disclaimer, the term of this patent is extended or adjusted under 35 U.S.C. 154(b) by 610 days.

(21) Appl. No.: 16/961,714

(22) PCT Filed: Oct. 23, 2018

(86) PCT No.: PCT/EP2018/078997
§ 371 (c)(1),
(2) Date: Jul. 13, 2020

(87) PCT Pub. No.: WO2019/137647
PCT Pub. Date: Jul. 18, 2019

(65) Prior Publication Data
US 2021/0055139 A1    Feb. 25, 2021

(30) Foreign Application Priority Data
Jan. 15, 2018  (DE) .................. 20 2018 100 186.8

(51) Int. Cl.
*G01D 11/26*  (2006.01)
*G01K 1/08*  (2021.01)
(Continued)

(52) U.S. Cl.
CPC ............. *G01D 11/26* (2013.01); *G01K 1/08* (2013.01); *G01K 7/16* (2013.01); *G01K 13/02* (2013.01);
(Continued)

(58) Field of Classification Search
CPC .......... G01D 11/26; G01K 1/08; G01K 13/02; G01K 7/16
See application file for complete search history.

(56) References Cited

U.S. PATENT DOCUMENTS

| 5,377,528 A | 1/1995 | Dauvergne |
| 5,631,638 A | 5/1997 | Kasper et al. |

(Continued)

FOREIGN PATENT DOCUMENTS

| CN | 104736980 A | 6/2015 |
| CN | 106662475 A | 5/2017 |

(Continued)

OTHER PUBLICATIONS

International Search Report for corresponding International Application No. PCT/EP2018/078997 dated Feb. 11, 2019.

*Primary Examiner* — Jamel E Williams
(74) *Attorney, Agent, or Firm* — Renner, Otto, Boisselle & Sklar, LLP

(57) ABSTRACT

A sensor module as well as a method for manufacturing a sensor module for determining a property of a fluid, in particular for measuring air quality, comprises a printed circuit board, at least one sensor on the printed circuit board for measuring a parameter of the surrounding air and a housing for the printed circuit board. A part of the printed circuit board protrudes from an opening in the housing (10), wherein the at least one sensor (21, 22) is located on a front side of the protruding part of the printed circuit board. In addition, at least the front side of the protruding part of the printed circuit board, with the exception of a recess for the at least one sensor, is encapsulated with a filling compound. The sensor module can be used in an interior or an air duct of motor vehicles or buildings. In one embodiment, the (Continued)

sensor module measures temperature, relative humidity and gas concentration in a fluid, especially in the surrounding air.

30 Claims, 8 Drawing Sheets

(51) Int. Cl.
    *G01K 7/16*     (2006.01)
    *G01K 13/02*     (2021.01)
    *G01N 25/66*     (2006.01)
    *G01N 27/12*     (2006.01)
    *G01N 33/00*     (2006.01)
    *G01K 13/024*     (2021.01)

(52) U.S. Cl.
    CPC ............ *G01N 25/66* (2013.01); *G01N 27/12* (2013.01); *G01N 33/0027* (2013.01); *G01K 13/024* (2021.01)

(56) References Cited

U.S. PATENT DOCUMENTS

| | | | | |
|---|---|---|---|---|
| 6,094,349 | A * | 7/2000 | Fassel | H05K 7/20454 |
| | | | | 361/728 |
| 6,341,892 | B1 * | 1/2002 | Schmermund | G01K 1/08 |
| | | | | 374/185 |
| 2002/0024164 | A1 * | 2/2002 | Boyes | F16J 15/14 |
| | | | | 264/46.7 |
| 2002/0048312 | A1 | 4/2002 | Schurr | |
| 2002/0069699 | A1 * | 6/2002 | Sato | G01F 5/00 |
| | | | | 73/204.22 |
| 2007/0071065 | A1 * | 3/2007 | Pils | G01K 5/42 |
| | | | | 374/E5.028 |
| 2008/0317093 | A1 * | 12/2008 | Mau | G01J 5/04 |
| | | | | 374/E13.003 |
| 2009/0245324 | A1 | 10/2009 | Sunaga et al. | |
| 2009/0295181 | A1 | 12/2009 | Lawlor et al. | |
| 2015/0000395 | A1 * | 1/2015 | Tashiro | G01F 1/6842 |
| | | | | 73/204.26 |
| 2015/0276503 | A1 | 10/2015 | Grun et al. | |
| 2016/0290893 | A1 * | 10/2016 | Itakura | G01F 5/00 |
| 2016/0356656 | A1 * | 12/2016 | Hoshika | F02M 35/10091 |
| 2017/0248455 | A1 | 8/2017 | Miki et al. | |
| 2018/0252564 | A1 * | 9/2018 | Tashiro | G01F 1/6842 |
| 2019/0041372 | A1 | 2/2019 | Wiget et al. | |

FOREIGN PATENT DOCUMENTS

| | | | | |
|---|---|---|---|---|
| DE | 1827060 | U | 2/1961 | |
| DE | 4321371 | A1 | 2/1994 | |
| DE | 4322937 | A1 | 1/1995 | |
| DE | 4414594 | A1 | 11/1995 | |
| DE | 29717626 | U1 | 2/1998 | |
| DE | 19734110 | C1 | 11/1998 | |
| DE | 10039576 | A1 | 2/2002 | |
| DE | 10261921 | A1 | 2/2004 | |
| DE | 10325971 | A1 | 12/2004 | |
| DE | 102005016896 | B3 | 10/2006 | |
| DE | 202013104451 | U1 | 11/2013 | |
| DE | 112013001060 | T5 | 11/2014 | |
| DE | 102014003199 | A1 * | 9/2015 | ........... B62D 25/105 |
| DE | 112014003199 | T5 | 4/2016 | |
| DE | 202018100186 | U1 | 1/2018 | |
| DE | 202018100186 | U1 * | 3/2018 | ............. G01D 11/24 |
| EP | 3176546 | A1 * | 6/2017 | ......... F02M 35/1038 |
| EP | 3557192 | A1 | 10/2019 | |
| JP | 2010043883 | A * | 2/2010 | ........... G01F 1/6842 |
| JP | 2012163505 | A * | 8/2012 | ........... F02D 41/187 |
| JP | 2016196857 | A | 11/2016 | |
| WO | 0129457 | A1 | 4/2001 | |
| WO | 2019201940 | A1 | 10/2019 | |

* cited by examiner

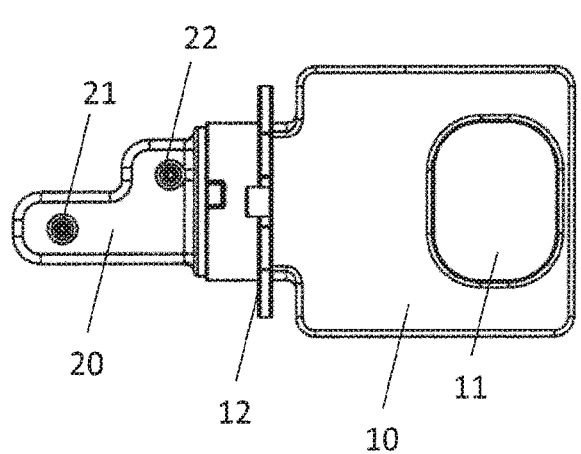
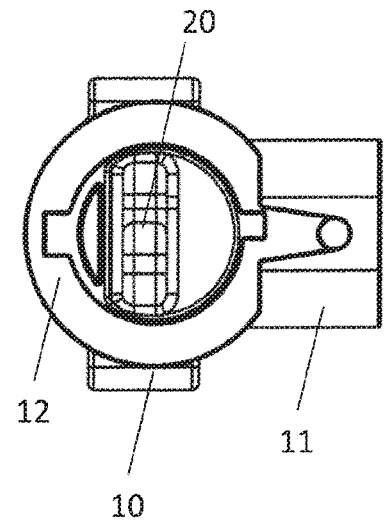
FIG. 1
FIG. 3
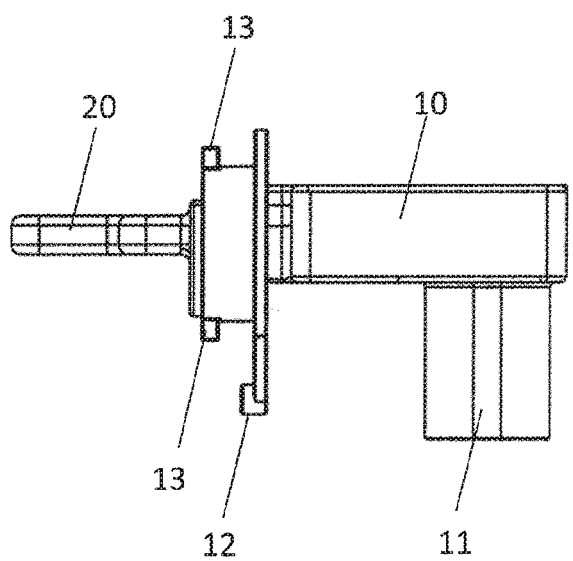
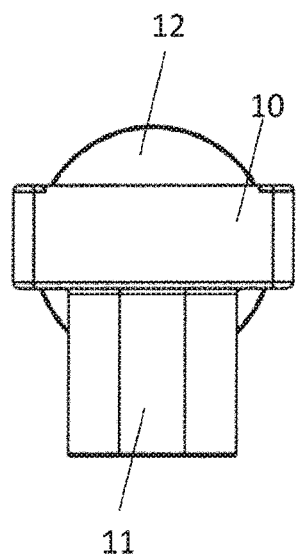
FIG. 2
FIG. 4

SENSOR MODULE FOR AIR QUALITY MEASUREMENT

This application is a national phase of International Application No. PCT/EP2018/078997 filed Oct. 23, 2018 and published in the German language, which claims priority to German Application No. DE 20 2018 100 186.8 filed Jan. 15, 2018, both of which are hereby incorporated herein by reference.

TECHNICAL FIELD

The invention relates to a sensor module and a method of manufacturing a sensor module for determining a property of a fluid, in particular for measuring air quality, in particular in an interior or an air duct of a motor vehicle or a building.

BACKGROUND ART

Sensor modules for air quality measurement measure various parameters that are considered characteristic for the quality of the surrounding air. These include temperature, relative humidity, aerosol concentration or a concentration of various gases such as ozone, nitrogen dioxide, sulphur dioxide or carbon monoxide. Sensor modules for air quality measurement are used to measure and monitor air parameters, e.g. in urban agglomerations. They are also used to measure air parameters in indoor areas, e.g. in buildings or motor vehicles. A special field of application is the air supply for such interiors, where the measured values of air parameters are used to control and create a pleasant climate in the interior. Sensor modules for air quality measurement are also used in outdoor air measurements, e.g. on buildings or motor vehicles.

Conventional sensor arrangements sometimes have large dimensions, comprise several, non-integrated individual sensors, are sensitive to mechanical damage or are difficult to install, require several chambers for measuring various air parameters or are inaccurate.

DISCLOSURE OF THE INVENTION

The present invention is based on the problem of eliminating the disadvantages of conventional sensor arrangements or providing an advantageous alternative sensor module. This task is solved by a sensor module according to claim 1 and by a method for manufacturing a sensor module according to claim 30.

The sensor module comprises a printed circuit board (PCB), at least one sensor on the printed circuit board for recording a parameter of a fluid, in particular of the surrounding air, and a housing for the printed circuit board. The fluid can be in gaseous state, or liquid state, or an aerosol.

A part of the circuit board protrudes from an opening in the housing, with at least one sensor located on a front side of the protruding part of the circuit board. At least the front side of the protruding part of the printed circuit board, with the exception of a recess for the at least one sensor, is encapsulated with a filling compound. Through the recess, the at least one sensor can be in direct contact with the fluid, for example with the surrounding air.

In addition to the front side, a back side of the protruding part of the printed circuit board opposite the front side may also be encapsulated with the filling compound, with the exception of a further recess opposite the at least one sensor. Alternatively, a part of the housing can at least partially support the back side of the PCB and be encapsulated with the PCB. In addition, at least the opening in the housing from which the printed circuit board protrudes can also be sealed with the filling compound.

In an embodiment, there is also at least one sensor on the back side of the circuit board.

The housing is preferably made of a solid material, especially plastic, e.g. PBT or PP, which makes the sensor module robust. The housing and the circuit board with at least one sensor are preferably manufactured individually and then assembled. When the printed circuit board is inserted into the housing, the part with the sensor for measuring air quality protrudes from the housing on one side, which is called the front side of the housing. Encapsulating the circuit board with filling compound reinforces the circuit board and seals it, creating a robust sensor module.

In addition, the encapsulation of the printed circuit board eliminates the need for a measuring chamber for the at least one sensor, which, due to the enclosed volume, would make the measurement on the one hand sluggish and on the other hand could lead to incorrect measurements due to accumulated outgassing from the sensor module itself. Thus, the present sensor module enables a fast and accurate measurement of the parameter to be determined, for example the air quality.

In an advantageous embodiment, a basic shape of the housing is cuboid. The cuboid part serves as a receptacle for the printed circuit board. Depending on the intended use and connection options, the housing can include other parts. Example parts are described below.

The housing preferably includes a connector via which the printed circuit board is electrically contacted from outside the sensor module. In an advantageous embodiment, the connector is a standard plug with electrical contacts, via which a power supply and a readout of the measurement data of at least one sensor are accomplished. The connector can be located, for example, on a side of the housing that is adjacent to or opposite the front side with the opening.

Furthermore, the housing may include a fastener for mounting, e.g. on an air duct or in a water tank. The air duct can be, for example, the air supply for an interior space or a pipe in a measuring system, which has an opening to accommodate the sensor module. The fastener is preferably located at the front side of the housing. Preferably the fastener has the form of a plug connection, e.g. a bayonet lock. The fastener is preferably shaped in such a way that in the operating position the part of the PCB with the at least one sensor protrudes into the air duct, while the connector is located outside the air duct.

The housing may include a further opening on a side adjacent to the front side with the first opening. The further opening can be used, for example, to simply insert the circuit board with the at least one sensor into the housing. In the finished state, the further opening is preferably also encapsulated with the filling compound.

Furthermore, the entire circuit board can be encapsulated with the filling compound, which allows for a compact and sealed sensor module, and which preferably takes place in one step, so that the encapsulation compound is formed in one piece. The only exceptions to this are a recess for the at least one sensor and a further recess opposite the at least one sensor, which is created due to the manufacturing process, as explained below. In another embodiment, part or all of the back side of the PCB may be covered by the housing.

Preferably the housing has guiding means for inserting the PCB through the further opening. In particular, the guiding means may include a chamfer for an oblique insertion of the PCB into the housing, the chamfer being arranged obliquely to the side with the further opening. When inserting the circuit board, care is taken to ensure that protruding components such as sensor chips on the circuit board are not damaged. Proper insertion is carried out with sufficient clearance to the chamfer. In the next step, the PCB is preferably pressed onto the chamfer. Finally, the PCB is tilted over the chamfer into its final position in the housing.

In addition, the housing may include locking means to lock the board in place after insertion. The locking means can be designed as a plastic clip in the housing and holds the PCB in its final position for the encapsulation step. It is also conceivable to weld or press a pin connected to the housing onto the circuit board or to solder or press a connector pin, which is firmly connected to the housing, onto the circuit board.

Preferably a sensor of the sensor module measures a temperature of a fluid, for example of the surrounding air. The temperature sensor may comprise, for example, a temperature-dependent electrical resistance. In another embodiment, a sensor measures a relative humidity of a fluid, for example of the surrounding air. In particular, the temperature sensor and the humidity sensor can be integrated in a single chip, which can, for example, determine a dew point of the surrounding air.

Temperature and relative humidity of the air are important parameters for air quality and a pleasant climate. Therefore, the sensor module is preferably used for measuring the air quality in an air duct or an interior, especially in a motor vehicle or building. In addition, a measured value can be used to control the climate in the interior, for example by controlling the air supply or air conditioning.

In another embodiment, a sensor of the sensor module is a gas sensor, which preferably measures a concentration of a gas in a surrounding fluid, for example in the surrounding air. The above-mentioned temperature sensor or the combination of temperature and humidity sensor can also be supplemented by such a gas sensor. The concentration of different gases can also be an important property or parameter of a fluid that needs to be determined, for example air quality. For example, an increased concentration of ozone, nitrogen dioxide, sulphur dioxide or carbon monoxide is harmful to health. Measured values from the gas sensor can therefore also be used to control the air supply or the air conditioning system. For example, the air supply from outside can be switched off if an increased concentration of harmful gases is detected in the air supply duct.

Preferably the sensor for measuring a gas concentration is a MOX (metal oxide) sensor. To reach the operating temperature such a sensor includes a heating element. In order not to tamper with the measurement of other parameters, e.g. the temperature, the gas sensor is mounted on the part of the PCB that protrudes from the housing, far away from the other sensors. A possible arrangement is that the other sensors protrude far into the air duct, while the gas sensor is close to the edge of the air duct.

For this purpose, the protruding part of the printed circuit board can be step-shaped and comprise two steps, whereby the two steps protrude from the housing by the lengths $l1$ and $l2$ and $l1>l2$. A distance of the gas sensor from the opening in the housing is then preferably at most 25% of $l1$, while a distance of the remaining sensors from the opening is preferably at least 75% of $l1$.

In an advantageous embodiment, the sensor module includes a power supply. The power supply is preferably mounted on the printed circuit board, receives the electrical current via the connector and supplies the sensor(s) with power.

In addition, the sensor module may include processing means for measured values from the at least one sensor. The processing means can for example perform a calibration of the measured values, a calculation of fused data from different sensors and/or averaging. It is also conceivable that certain thresholds are implemented, and if the measured values exceed or fall below these thresholds, a warning signal is issued, for example if a threshold for the concentration of a harmful gas in the air is exceeded. The processing means is also powered by the power supply and the measured and/or processed data are provided via the connector.

In addition, the sensor module may include at least one electrostatic discharge (ESD) bracket made of an electrically conductive material on the printed circuit board, which spatially bridges the at least one sensor at least partially. The ESD bracket is connected to a ground connection on the printed circuit board and protects the at least one sensor from damage by electrostatic discharge. In various embodiments, the ESD bracket is fixed to the circuit board at only one point or it is connected to the circuit board on two opposite sides of the sensor, for example. In an advantageous embodiment, there is a distance, e.g. in the order of 0.1 mm, between the ESD bracket and the sensor, which allows the sensor to be in direct contact with the surrounding air. In particular, an ESD bracket is envisaged, which extends over the entire sensor in terms of surface area, but has a hole at the location of the sensitive element to allow air contact for the sensor. Preferably, the ESD bracket is partially encapsulated on the printed circuit board with filling compound, which increases the robustness and service life of the sensor module.

Various embodiments are conceivable for the filling compound. Preferably the filling compound is a hot melt, e.g. Henkel Technomelt PA 6771 or Bostik Thermelt 181, or a UV-curable adhesive. These have the advantage that they do not have to be applied under high pressure, thus avoiding damage to the sensor during encapsulation. However, other adhesives, casting compounds or resins are also conceivable. For example, a common injection molding can be used, if the components allow it.

A further aspect of the present invention is a method of manufacturing a sensor module for determining a property of a fluid, for example for air quality measurement, comprising the following steps. (a) A printed circuit board is provided with at least one sensor which measures a parameter of the surrounding fluid, for example of the surrounding air; furthermore, a housing for the printed circuit board is provided which has an opening for a protruding part of the printed circuit board at least on one side. (b) The printed circuit board is inserted into the housing. (c) A front side, on which the at least one sensor is located, of the protruding part of the printed circuit board is encapsulated with a filling compound, except for a recess for the at least one sensor. Such a manufacturing process has the advantage that the individual parts are provided in modular form and can be easily assembled. Encapsulation produces a sealed and mechanically robust sensor module.

In an advantageous embodiment of the method, the printed circuit board is inserted in step b through a further opening in the housing. In addition, the insertion of the PCB in step b can be supported by a guiding device and/or a chamfer in the housing. This ensures easy assembly of the sensor module and at the same time ensures that the printed circuit board is seated at a designated position in the housing.

Furthermore, step b preferably includes the following steps: the printed circuit board is inserted into the housing at an angle through the further opening, wherein a distance of the printed circuit board from the chamfer in the housing is kept greater than the height of the at least one sensor together with an ESD bracket above the printed circuit board; this process is preferably assisted by the guiding means. When the part of the printed circuit board with the at least one sensor protrudes from the housing through the opening, the printed circuit board can be pressed onto the chamfer, preferably assisted by the guiding means. The PCB can be tilted over the chamfer to a final position where it is preferably locked in the housing by locking means.

In step c, in an advantageous embodiment, additionally a back side of the protruding part of the circuit board opposite the front side is encapsulated with filling compound, with the exception of a further recess opposite the at least one sensor. In step c, the opening in the housing can also be encapsulated with filling compound. It is also advantageous that in step c additional cavities in the housing and in the circuit board together with the at least one sensor are filled, so that only one recess and one further recess for the at least one sensor as well as possible cavities in the at least one sensor remain. This further increases the robustness of the sensor module.

Preferably, in step c, the housing together with the inserted printed circuit board is transferred for encapsulation into a mould which has a punch for the recess for the at least one sensor. The punch can exert a force on an ESD bracket above the at least one sensor and deform it before the encapsulation. It is advantageous that a further stamp exerts a counterforce on the back side of the PCB opposite the ESD bracket such that it is not deformed or damaged.

In an advantageous embodiment, the filling compound is a hot melt or UV-curable adhesive.

As is obvious to the skilled person, synergistic effects can arise from the combination of features of different embodiments and aspects. Although these may not be described in detail, they are expressly included in the disclosure of this document.

BRIEF DESCRIPTION OF THE DRAWINGS

Further advantageous embodiments of the invention result from the dependent claims and the modes for carrying out the invention shown below on the basis of the drawings, which show:

FIG. 1 a top view of a sensor module for determining a property of a fluid, for example for air quality measurement, with a temperature/humidity and a gas sensor on the front side of a printed circuit board according to a first embodiment of the invention, FIG. 2 a side view of the sensor module according to the first embodiment, FIG. 3 a front view of the sensor module according to the first embodiment, FIG. 4 a view from behind on the sensor module according to the first embodiment, FIGS. 5 and 6 two perspective views of the sensor module according to the first embodiment from different angles, FIG. 7 a top view of a sensor module for determining a property of a fluid, for example for air quality measurement, with a temperature/humidity sensor on the front side of a printed circuit board according to a second embodiment of the invention, FIG. 8 a top view of a sensor module for determining a property of a fluid, for example for air quality measurement, with a temperature/humidity sensor on the front side of a printed circuit board according to a third embodiment of the invention, FIGS. 9 and 10 a side view of a vertical cut through the housing of the sensor module, while a printed circuit board with a sensor is inserted at an angle during manufacture according to an embodiment.

MODES FOR CARRYING OUT THE INVENTION

Figure 5:
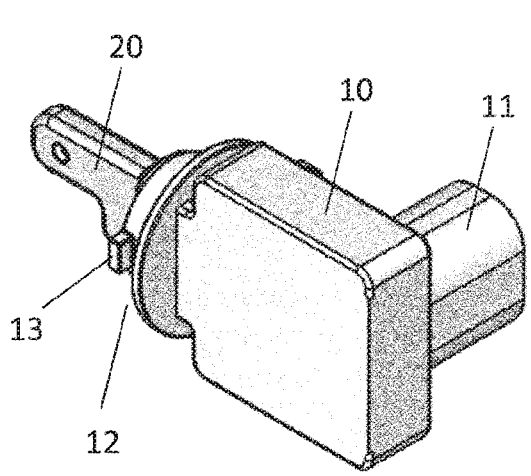

FIG. 1 shows a top view of a sensor module for determining a property of a fluid, for example for air quality measurement, with a temperature/humidity sensor 21 and a gas sensor 22 on the front side of a printed circuit board 20 according to a first embodiment of the invention. The sensor 21 is an integrated sensor for measuring the temperature and relative humidity in the surrounding air. The gas sensor 22 is a MOX (metal oxide) sensor which preferably measures the concentration of a gas, e.g. of NO2, SO2, O3, CO, VOC (volatile organic compounds), in the surrounding air.

The two sensors 21 and 22 are mounted on a printed circuit board 20 and are supplied with power via this board. The printed circuit board 20 is encapsulated with a filling compound for reinforcement and sealing, preferably with a hot melt, e.g. Henkel Technomelt PA 6771 or Bostik Thermelt 181. The encapsulation has recesses in the sensors 21 and 22 so that the surrounding air can come into contact with the sensitive elements. It can be seen from FIG. 1 that the sensors 21 and 22 are not surrounded by measuring chambers, but are directly exposed to the surrounding fluid, e.g. the surrounding air, e.g. the air flow in an air supply duct. This has the advantages that the measurement is not delayed by a sluggish fluid/air exchange in the chamber, and that the measurement is not distorted by outgassing that could accumulate in a chamber.

In the embodiment shown, the temperature/humidity sensor 21 is positioned near the tip of the PCB, while the gas sensor 22 is located near the housing 10. Thus, the two sensors 21 and 22 are clearly separated from each other, which prevents mutual interference, in particular a tampering of the temperature measurement by a heating element in the gas sensor 22.

A power supply and a data processing unit for the measured values are also mounted on circuit board 20 (both not shown because they are located inside housing 10). These are located on that part of the printed circuit board 20 which does not protrude from the housing 10. The housing is made of plastic, e.g. PP or PBT, and protects the sensor module from mechanical damage. The connection of the sensor module to an external power supply and further processing of the data is done via electrical contacts in a connector 11. In the embodiment shown in FIG. 1, the connector 11 is formed on a side of the housing 10 defined as top side, while the printed circuit board 20 protrudes from the housing 10 on a side defined as front side. Different arrangements are possible, e.g. the connector 11 is located on a back side of housing 10 opposite the front side.

Another part of the housing 10 in FIG. 1 is the bayonet lock 12 for mounting the sensor module on a carrier, e.g. for attachment to an air supply duct for the interior of a motor vehicle or building. By fastening with a bayonet lock 12, an airtight connection can be established with simultaneous locking of the sensor module in the carrier. However, other forms of fastening are also possible, e.g. via a thread.

FIG. 2 shows a side view of the sensor module according to the first embodiment, while FIG. 3 illustrates a front view and FIG. 4 a back view. FIG. 2 shows how the printed circuit board 20 with the sensors at the front protrudes from the housing 10. In addition, the bayonet lock 12 with two pins 13 for locking is illustrated. The view of FIG. 4 from the back is the view of a viewer looking at the mounted sensor module from outside the air supply duct.

FIG. 5 shows a perspective view of the sensor module with housing 10 and encapsulated circuit board 20 from diagonally below according to the first embodiment of FIGS. 1-4, with the pin 13 of the bayonet connection 12 clearly visible.

Figure 6:
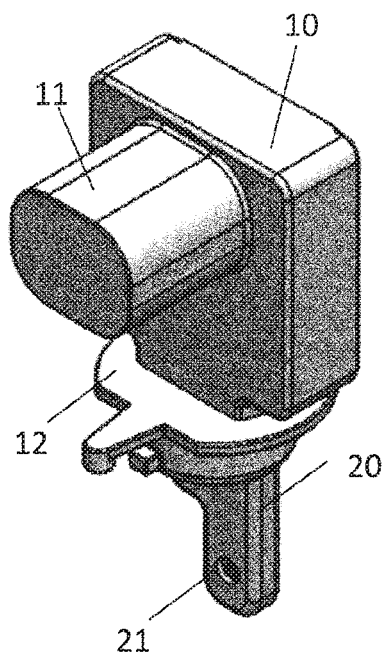

FIG. 6 supplements this with a perspective view from an oblique angle. In this view, the recess can be seen, which is located in the encapsulation around the circuit board 20 above the sensor 21 and allows direct contact of a sensitive element of the sensor 21 with the surrounding fluid, for example the surrounding air.

Figure 7:
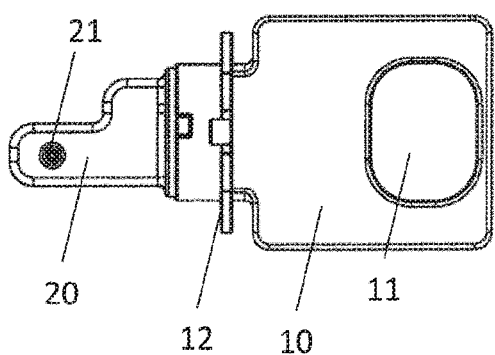

FIG. 7 shows a top view of a sensor module for determining a property of a fluid, for example for air quality measurement, with a temperature/humidity sensor on the front side of a printed circuit board 20 according to a second embodiment of the invention. The second embodiment comprises to a large extent the same components as the first embodiment in FIGS. 1-6, i.e. a housing 10 with protrusions for a connector 11 and a bayonet lock 12, and an encapsulated printed circuit board 20. In contrast to FIGS. 1-6, FIG. 7 shows only one sensor 21. In one embodiment, this is again an integrated temperature/humidity sensor.

Figure 8:
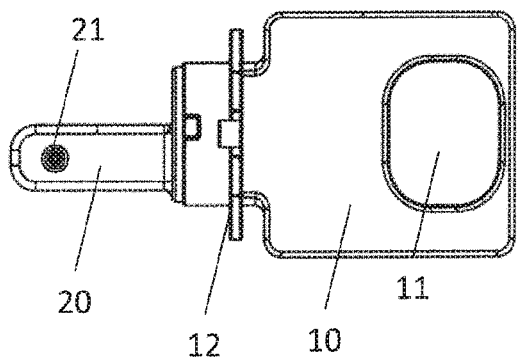

FIG. 8 illustrates a top view of a sensor module for determining a property of a fluid, for example for air quality measurement, with a temperature/humidity sensor on the front side of a printed circuit board 20 according to a third embodiment of the invention. The difference to the first two embodiments in FIGS. 1-6 and 7 is the shape of the encapsulated printed circuit board 20. The part of the printed circuit board 20 which protrudes from the housing and thus into the air supply duct in the assembled state is less wide in FIG. 8. This leads to a lower influence on the air flow in the duct or the fluid to be measured. As in the second embodiment, an integrated temperature/humidity sensor is preferably mounted on PCB 20. However, it is also conceivable for all embodiments to use only a single temperature sensor if the relative humidity values are not of interest.

FIGS. 9-12 show a side view of a housing 10 of the sensor module during manufacture, while a printed circuit board 20 with a sensor 23 is inserted before encapsulation according to an embodiment. The housing 10 with protrusions for connector 11 and bayonet lock 12 including pin 13 corresponds largely to that shown in FIG. 2. In addition, FIGS. 9-12 shows a chamfer 14, the purpose of which is explained in the following.

The circuit board 20 is not yet encapsulated in FIGS. 9-12. Therefore, the sensor 23 is visible as an attached chip. Furthermore, the sensor 23 is spanned by an ESD bracket 24 (electrostatic discharge) which protects it from damage by electrostatic discharge. The ESD bracket 23 is also largely encapsulated after encapsulation, which increases the mechanical stability of the sensor module.

Figure 9:
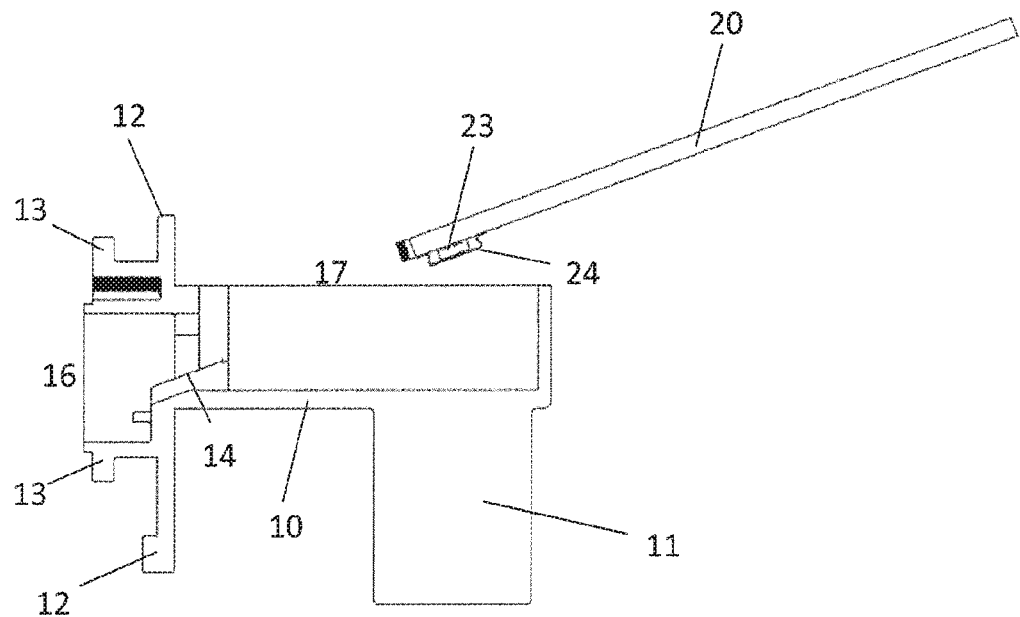
Figure 10:
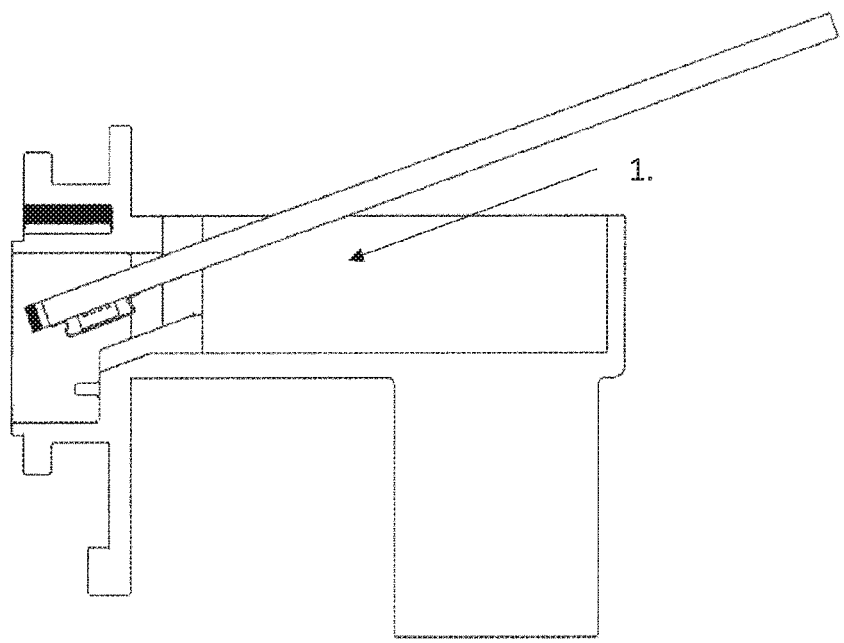
Figure 11:
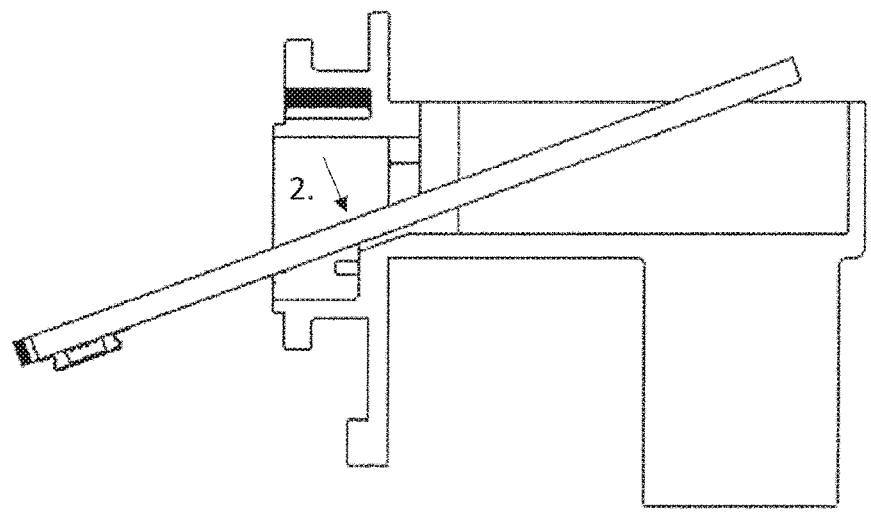
FIG. 11 shows a vertical cut through the housing, while the printed circuit board with the sensor is pressed onto a chamfer during manufacture according to an embodiment.

As the sensor 23 and the ESD bracket 24 can easily be damaged before encapsulation, the printed circuit board 20 is inserted at an angle and with sufficient distance to the chamfer 14 in the first assembly step in FIG. 9, so that the sensor 23 and the ESD bracket 24 do not touch the chamfer 14. In FIG. 10, it is shown how the printed circuit board 20 is pushed out of the opening 16 in the front of the housing 10 such that the part of the printed circuit board 20 with the sensor 23 in FIG. 11 protrudes from the housing 10. The printed circuit board 20 is guided by guiding means 15, which is shown in FIG. 13. In FIG. 11, the printed circuit board is then pressed against the chamfer 14. The insertion of the printed circuit board 20 is completed in FIG. 12 by tilting it over the chamfer 14 and thus, with the exception of the part with the sensor 23 protruding at the front, it is situated completely in the housing 10.

Figure 12:
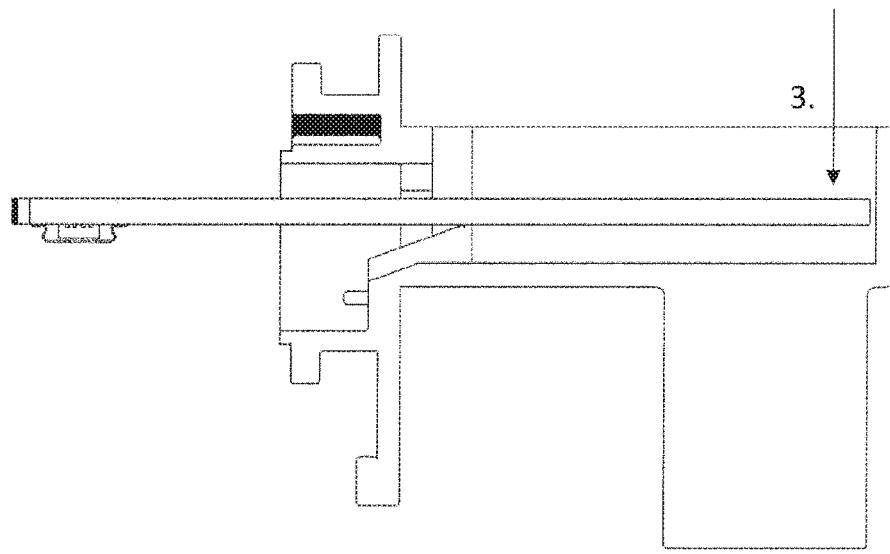
FIG. 12 shows a vertical cut through the housing, while the printed circuit board with the sensor is tilted over the chamfer into its final position during manufacture according to an embodiment, FIG. 13 a view from below onto a horizontally cut sensor module for determining a property of a fluid, e.g. for air quality measurement, with guiding means and alignment pins for the circuit board, FIGS. 14, 15 and 16 a vertical cut through the housing with different embodiments of locking means for the printed circuit board, FIGS. 17 and 18 a vertical cut through the housing with two variants of mounting a connector, FIG. 19 a top view of the sensor module with marking of a vertical cut A-B through the circuit board for the following Figs., FIGS. 20, 21 and 22 the vertical cut A-B through the printed circuit board.
Figure 13:
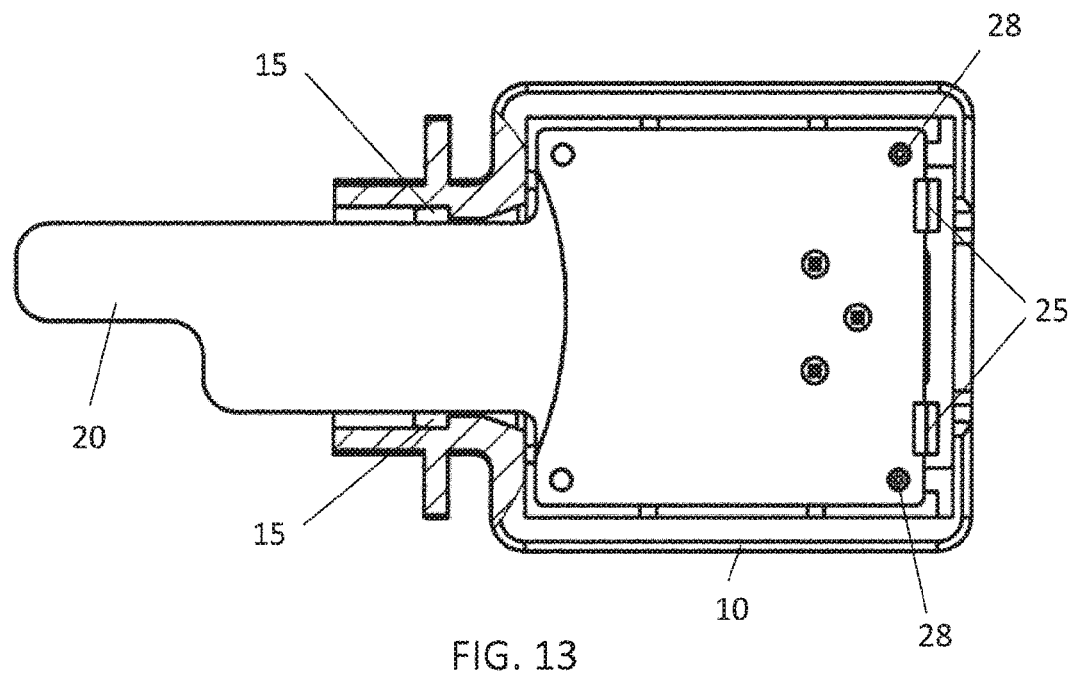

Finally, the arrangement shown in FIG. 12 is encapsulated. For this purpose, the entire arrangement is placed in a mould in vertical orientation as shown in FIG. 1. The mould includes a punch for each sensor, which keeps the recess for the sensor free. Now the further opening 17 of the housing 10, through which the PCB 20 in FIGS. 9-11 was inserted, is filled and the part of the PCB 20 protruding from the opening 16 is encapsulated with the sensor 23 and the ESD bracket 24 with the exception of the recess.

Various materials can be used as filling material, but a hot melt is preferred. The advantage of a hot melt is that lower pressures have to be applied during encapsulation than with other methods such as injection moulding. However, UV-curable resins are also conceivable as a filling material. At the end of the production process, a compact and robust sensor module is produced.

FIG. 13 shows a view from below onto a horizontally cut sensor module for determining a property of a fluid, for example for air quality measurement. The printed circuit board 20 is secured against lateral displacement in the housing 10 by the guiding means 15. In addition, the guiding means 15 support the insertion process described above. Furthermore, two alignment pins 28 help to align the PCB 20 correctly and clamps 25 serve as locking device for the PCB 20 in the desired position.

Figure 14:
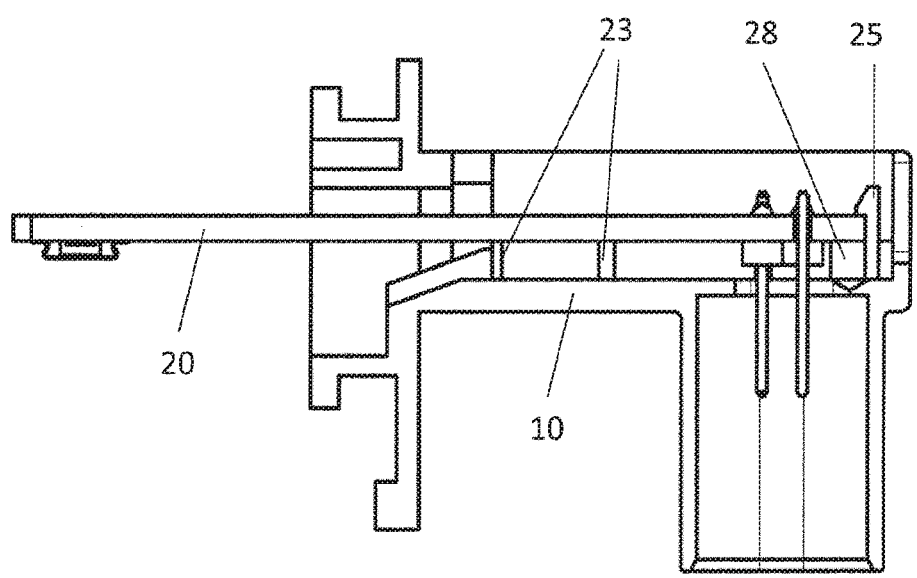
Figure 15:
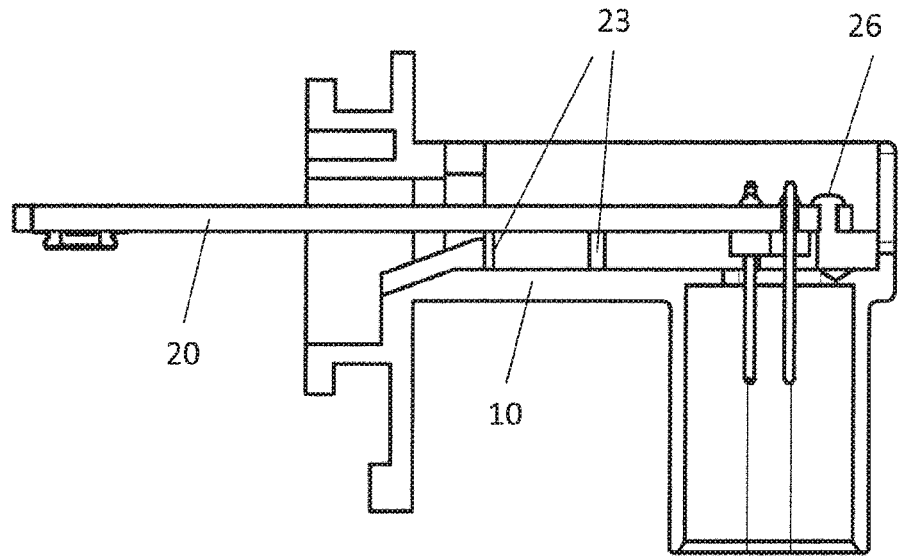
Figure 16:
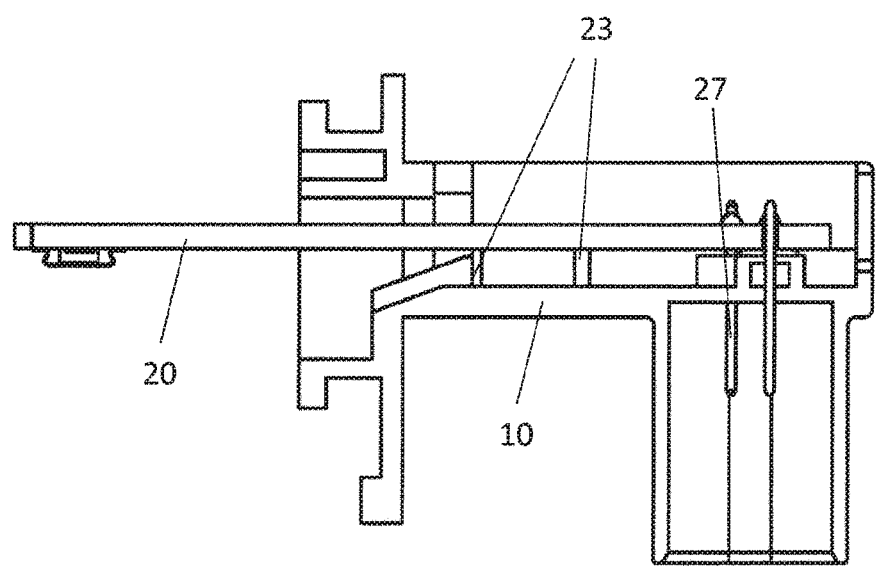

FIGS. 14, 15 and 16 illustrate a vertical cut through the housing 10 with different embodiments of the locking means for the printed circuit board 20, with the printed circuit board 20 being supported vertically by supports 23. Towards the bottom, the clamps 25 are used to hold the PCB 20, see FIG. 14. In FIG. 15, a pin 26 is used to lock the PCB 20 at the bottom. In FIG. 16, the locking downwards is achieved by soldering or pressing a pin 27 of the connector 11, which is fixed in the housing 10, to the printed circuit board 20.

Figure 17:
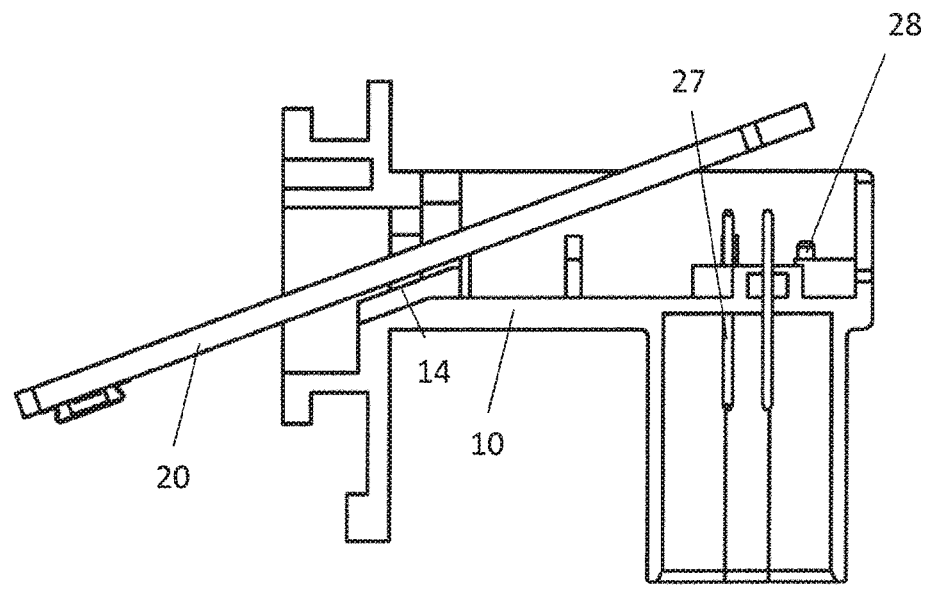
Figure 18:
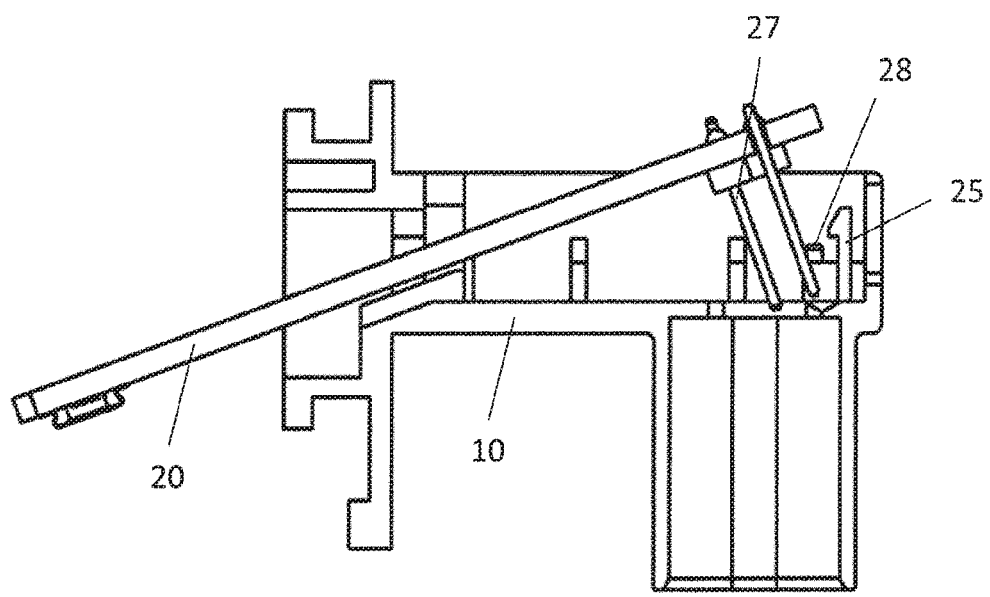

FIGS. 17 and 18 show a vertical cut through the housing with two variants for attaching pins 27 of a connector 11. In FIG. 17, the pins 27 are already firmly mounted in the housing 10 before the PCB 20 is inserted into the housing 10. When tilting the PCB over the chamfer 14, the pins 27 then pierce the PCB 20 in holes provided for this purpose in the PCB 20. Finally, the pins 27 are soldered to the PCB 20 or already fixed by pressing them in.

In FIG. 18, the pins 27 are already soldered to the PCB 20 or pressed into the PCB 20 before the PCB 20 is inserted into the housing 10. When tilting the printed circuit board 20 over the chamfer 14, they are inserted into the connector 11 up to their desired position.

Figure 19:
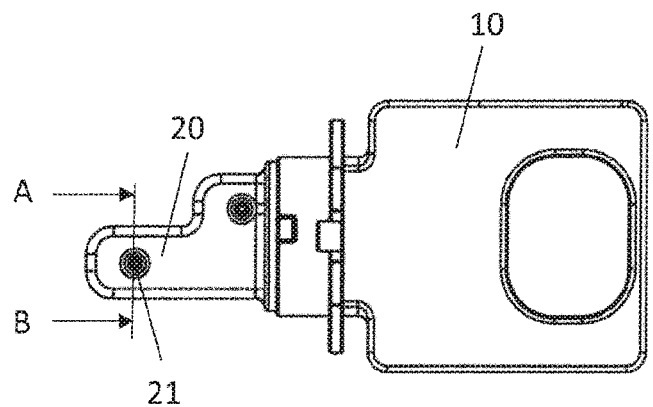
Figure 20:
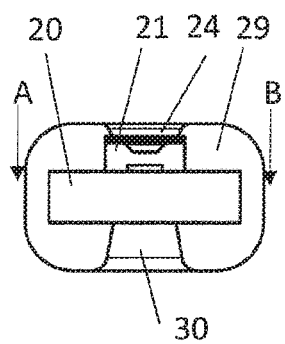
Figure 21:
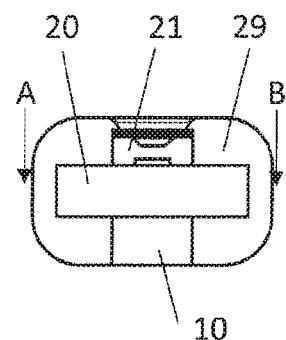
Figure 22:
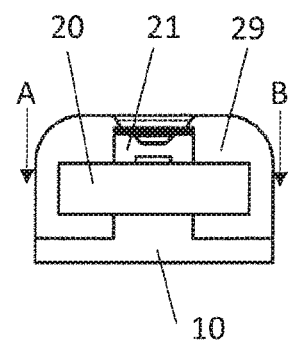

FIG. 19 shows a top view of the sensor module with housing 10 and printed circuit board 20 as well as marking of a vertical section A-B through the printed circuit board 20. FIGS. 20, 21 and 22 show different embodiments of encapsulating the printed circuit board 20 with the filling compound 29 by vertical sections A-B through the printed circuit board 20. In the embodiment of FIG. 20, the complete circuit board 20 is encapsulated with filling compound 29 with the exception of a recess for the sensor 21 on the front side and a further recess 30 on the back side. The further recess is opposite the sensor 21 and comes from a further punch which exerts a counterpressure on the back side of the circuit board 20 when the circuit board 20 is encapsulated with the filling compound 29, while on the front side a punch exerts pressure on the ESD bracket 24.

In the embodiments of FIGS. 21 and 22, there is no further recess opposite the sensor 21 on the back side of the printed circuit board 20, but part of the housing 10 is continuous along the printed circuit board 20 all the way up to this point. This part of the housing supports the protruding part of the printed circuit board 20 and thus makes the sensor module more robust. In FIG. 21, the lateral extension of this housing part along the section A-B is limited to the width of the opposite sensor 21. In FIG. 22, the housing part in section A-B has the shape of an upside down "T" whose width exceeds the width of the printed circuit board 20. The cavity between the cross line of the "T" and the printed circuit board 20 is filled with filling compound 29 during encapsulation. This arrangement makes the protruding part of the PCB 20 even less sensitive to mechanical influences.

The invention claimed is:

1. Sensor module for determining a property of a fluid, in particular for measuring air quality, comprising
a printed circuit board,
at least one sensor on the printed circuit board for recording a parameter of the fluid, in particular of the surrounding air, and
a housing for the circuit board,
wherein a part of the circuit board protrudes from an opening in the housing,
wherein the at least one sensor is located on a front side of the protruding part of the printed circuit board,
wherein at least the front side of the protruding part of the printed circuit board, with the exception of a recess for the at least one sensor, is encapsulated with a filling compound,
the housing comprising a further opening on a side adjacent to or opposite the side with the first opening.

2. Sensor module according to claim 1, wherein at least a back side of the protruding part of the printed circuit board, with the exception of a further recess which is opposite the at least one sensor, is encapsulated with filling compound.

3. Sensor module according to claim 1, wherein at least the opening in the housing is encapsulated with filling compound.

4. Sensor module according to claim 1, the housing being of plastic material.

5. Sensor module according to claim 1, wherein a base shape of the housing is cuboidal.

6. Sensor module according to claim 1, the housing comprising a connector for electrically contacting the printed circuit board from outside the sensor module.

7. Sensor module according to claim 6, wherein the connector is located on a side of the housing adjacent to or opposite the side with the opening.

8. Sensor module according to claim 1, the housing comprising a fastener for mounting on an air duct or in a water tank.

9. Sensor module according to claim 8, wherein the fastener is located on the side of the housing with the opening.

10. Sensor module according to claim 8, the fastener comprising a bayonet lock.

11. Sensor module according to claim 1, wherein the further opening is encapsulated with filling compound.

12. Sensor module according to claim 1, wherein the entire printed circuit board, with the exception of a recess for the at least one sensor and a further recess opposite the at least one sensor, is encapsulated with filling compound.

13. Sensor module according to claim 1, the housing comprising guiding means for inserting the printed circuit board through the further opening into the housing.

14. Sensor module according to claim 13, the guiding means comprising a chamfer in the housing, which is arranged obliquely to the side with the further opening.

15. Sensor module according to claim 1, the housing comprising locking means for locking the circuit board after insertion.

16. Sensor module according to claim 1, wherein the at least one sensor is in direct contact with the surrounding air.

17. Sensor module according to claim 1, wherein the at least one sensor comprises a temperature sensor.

18. Sensor module according to claim 1, wherein the at least one sensor comprises a humidity sensor.

19. Sensor module according to claim 1, wherein the at least one sensor comprises a gas sensor.

20. Sensor module according to claim 19, wherein the gas sensor measures a concentration of a gas in the surrounding air.

21. Sensor module according to claim 19, wherein the gas sensor is a MOX sensor.

22. Sensor module according to claim 1, wherein the protruding part of the printed circuit board is step-shaped and comprises two steps,
wherein the two steps protrude from the housing by the lengths l1 and l2, where l1>l2.

23. Sensor module according to claim 22, wherein the at least one sensor comprises (i) a gas sensor and (ii) a temperature sensor and/or a humidity sensor,
wherein a distance of the gas sensor from the opening in the housing is at most 25% of l1, and
wherein a distance of the temperature sensor and/or the humidity sensor from the opening in the housing is at least 75% of l1.

24. Sensor module according to claim 1, comprising processing means for measured values from the at least one sensor on the printed circuit board.

25. Sensor module according to claim 1, comprising at least one ESD bracket made of an electrically conductive material on the printed circuit board, which at least partially spatially bridges the at least one sensor and is connected to a ground connection of the printed circuit board, for protecting the sensor from damage by electrostatic discharge.

26. Sensor module according to claim 25, wherein the ESD bracket is partially encapsulated with filling compound.

27. Sensor module according to claim 1, where the filling compound is a hot melt or UV curable adhesive.

28. Sensor module according to claim 17, wherein the at least one sensor comprises a humidity sensor, and wherein the temperature sensor and the humidity sensor are integrated in a single chip.

29. A sensor module for determining a property of a fluid, in particular for measuring air quality, comprising
- a printed circuit board,
- at least one sensor on the printed circuit board for recording a parameter of the fluid, in particular of the surrounding air, and
- a housing for the circuit board,
- wherein a part of the circuit board protrudes from an opening in the housing,
- wherein the at least one sensor is located on a front side of the protruding part of the printed circuit board,
- wherein at least the front side of the protruding part of the printed circuit board, with the exception of a recess for the at least one sensor, is encapsulated with a filling compound,
- comprising at least one ESD bracket made of an electrically conductive material on the printed circuit board, which at least partially spatially bridges the at least one sensor and is connected to a ground connection of the printed circuit board, for protecting the sensor from damage by electrostatic discharge.

30. A sensor module for determining a property of a fluid, in particular for measuring air quality, comprising
- a printed circuit board,
- at least one sensor on the printed circuit board for recording a parameter of the fluid, in particular of the surrounding air, and
- a housing for the circuit board,
- wherein a part of the circuit board protrudes from an opening in the housing,
- wherein the at least one sensor is located on a front side of the protruding part of the printed circuit board,
- wherein at least the front side of the protruding part of the printed circuit board, with the exception of a recess for the at least one sensor, is encapsulated with a filling compound,
- wherein in addition at least the opening in the housing is encapsulated with filling compound,
- where the filling compound is a hot melt or UV curable adhesive.

\* \* \* \* \*